US006281247B1

(12) United States Patent
Jessen

(10) Patent No.: US 6,281,247 B1
(45) Date of Patent: Aug. 28, 2001

(54) SALT FORMS OF (2E)-5-AMINO-5-METHYLHEX-2-ENOIC ACID N-METHYL-N-((1R)-1-(N-METHYL-N-((1R)-1-(METHYLCARBAMOYL)-2-PHENYLETHYL)CARBAMOYL)-2-(2-NAPHTHYL)ETHYL)AMIDE

(75) Inventor: Claus Ulrich Jessen, Vanloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/256,427

(22) Filed: Feb. 23, 1999

Related U.S. Application Data
(60) Provisional application No. 60/077,242, filed on Mar. 9, 1998.

(30) Foreign Application Priority Data
Mar. 3, 1998 (DK) ..................................... 0282/98

(51) Int. Cl.[7] ........................... A01N 37/18; A01N 31/16; C07C 233/05; C07C 235/76; C07C 237/22
(52) U.S. Cl. ......................................... 514/616; 564/153
(58) Field of Search ............................. 564/153; 514/616

(56) References Cited

FOREIGN PATENT DOCUMENTS
WO 97/23508    7/1997   (WO).

OTHER PUBLICATIONS
Database CAPLUS on STN, Acc. No. 1998:1384, Eriksen et al., 'Growth hormone component and bone anti–responsive agent in cyclic (coherence) treatment of osteoporosis.' WO 9746252 (abstract), 1997.*
Database CAPLUS on STN, Acc. No. 1995:982969, Robinson et al., 'Discovery of the hemifumarate and alpha–L–alanyloxy methyl ester as produrgs of an antirheumatic oxindole: Prodrugs for the enolic OH Group.' J. Med. Chem. (1996), 39(1), pp. 10–18 (abstract), 1996.*

Database CAPLUS on STN, Acc. No. 1991:435717, Sommermeyer et al., 'Pharmaceutical formulations containing nonhygroscopic carnitine mandelate.' DE 3841664 (abstract), 1991.*

* cited by examiner

Primary Examiner—Johann Richter
Assistant Examiner—Brian J. Davis
(74) Attorney, Agent, or Firm—Reza Green, Esq.

(57) ABSTRACT

The compounds disclosed are salts of (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide of Formula I

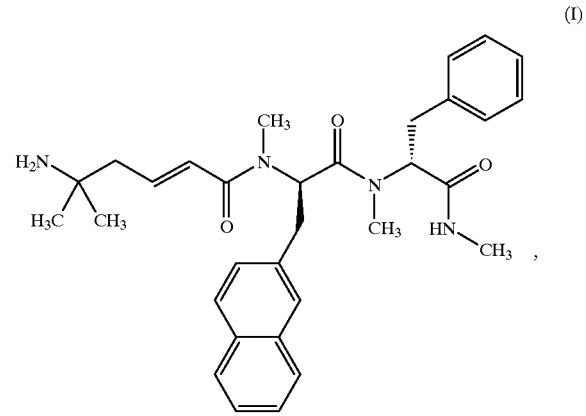

which have an aqueous solubility of at least 5 mg/ml, and a hygroscopicity of less than about 8 at 98% RH. These compounds are useful in the treatment of growth hormone deficiency.

11 Claims, No Drawings

SALT FORMS OF (2E)-5-AMINO-5-METHYLHEX-2-ENOIC ACID N-METHYL-N-((1R)-1-(N-METHYL-N-((1R)-1-(METHYLCARBAMOYL)-2-PHENYLETHYL)CARBAMOYL)-2-(2-NAPHTHYL)ETHYL) AMIDE

CROSS-REFERENCE TO RELATED APPLICATIONS

This application claims priority under 35 U.S.C. 119 of Danish application 0282/98 filed Mar. 3, 1998, and U.S. Provisional application 60/077,242 filed Mar. 9, 1998, the contents of which are fully incorporated herein by reference.

FIELD OF THE INVENTION

This invention relates to salt forms of (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide, preparation thereof and use as therapeutic agent.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilisation and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

The compound, (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide, was disclosed in WO 97/23508. Therein the hydrochloride salt was prepared.

For commercial use it is important to have a physiologically acceptable salt with good stability, good solubility, non-hygroscopicity, good bioavailability, good handling properties, and a reproducible crystalline form.

SUMMARY OF THE INVENTION

The present invention relates to a salt of (2E)-5-amino-5-methylhex-2-enoic acid N-methyl-N-((1)-1-(N-methyl-N-((1R)-1-(methylcarbamoyl)-2-phenylethyl)carbamoyl)-2-(2-naphthyl)ethyl)amide having an aqueous solubility of at least about 5 mg/ml, and a hygroscopicity of less than about 8 at 98% RH. In particular the invention relates to the anhydrous hemi fumarate salt of (2E)-5-amino-5-methylhex-2-enoic acid N-methyl-N-((1R)-1-(N-methyl-N-((1R)-1-methylcarbamoyl)-2-phenylethyl)carbamoyl)-2-(2-naphthyl)ethyl)amide. (The invention also relates to the hydrous hemi fumarate salt of (2E)-5-amino-5-methylhex-2enoic acid N-methyl-N-((1)-1-(N-methyl-N-((1R)-1-(methylcarbamoyl)-2-phenylethyl)carbamoyl)-2-(2-naphthyl)ethyl)amide and the L(+)-mandelate salt of (2E)-5-amino-5-methylhex-2-enoic acid N-methyl-N-((1R)-1-(N-methyl-N-((1)-1-(methylcrbamoyl)-2-phenylethyl)carbamoyl)-(naphthyl)ethyl)amide.

DETAILED DESCRIPTION OF THE INVENTION

The present invention relates to a salt of (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide having the structural formula I as shown herein below Formula I

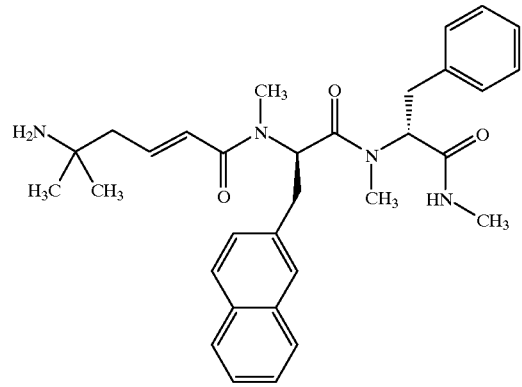

having an aqueous solubility of at least about 5 mg/ml, and a hygroscopicity of less than about 8 at 98% relative humidity (RH). Such aqueous solubility and hygroscopicity are measured by methods well-known in the art.

Hereinafter the above compound of formula I is referred to as compound I.

A salt of the compound I is provided in the form of polymorph crystals, which have good stability characteristics, good solubility in e.g. water, good bioavailability, good handling properties, and a reproducible crystalline form.

In one embodiment the salt of compound 1 has an aqueous solubility of at least about 7 mg/ml, preferably at least about 100 mg/ml, more preferably at least about 200 mg/ml, in particular from 5 to 400 mg/ml, such as 150 to 250 mg/ml.

In a further embodiment the salt of compound I has a hygroscopicity of less than about 7 at 98% RH, preferably from 0.1 to 8 at 98% RH, in particular from 0.5 to 7 at 98% RH, such as 1 to 6.5 at 98% RH.

In a further embodiment the salt of compound I is the hemi fumarate salt. In a further embodiment the salt of compound I is the hemi fumarate, monohydrate salt. In a further embodiment the salt of compound I is the L(+)-mandelate salt.

The present invention also provides a process for the preparation of a salt of compound I, which process comprises dissolving compound I in a suitable solvent, and dissolving a specific acid, in the same kind of solvent, and adding the solution of the acid to the solution of compound I, and crystallizing the resulting salt from the solution.

Examples of the common solvents include but are not limited to organic solvents in particular lower aliphatic alcohols such as ethanol, 2-propanol, 2-butanol, 1-hexanol and solvents like acetone, isobutylmethylketone and tetrahydrofuran. Preferred solvents are ethanol, 2-propanol and acetone. The mixture of the components are conveniently performed at temperatures from 40° C. to reflux before cooling down to 0–5° C. and collection of the crystals by filtration. The speed of cooling down may have influence on the type of salt obtained. Optionally, seeding crystals are added if precipitation has not occured within 1–2 hours after mixing.

The present invention also provides a pharmaceutical composition comprising a salt of compound I optionally together with a pharmaceutically acceptable carrier or diluent.

A salt of compound I may be used in human and veterinary medicine for stimulating the release of growth hormone. The present invention provides thus according to another aspect a method for stimulating the release of growth hormone in a patient such as a mammal, e.g. a human, comprising administering a therapeutically effective amount of a salt of compound I according to the invention.

A salt of (2E)-5-amino-5-methylhex-2-enoic acid N-methyl-N-((1)-1-(N-methyl-N-((1R)-1-(methylcarbamoyl)-2-phenylethyl)carbamoyl)-2-(2-naphthyl)ethyl)amide is useful for stimulation of growth hormone release in the elderly; prevention of catabolic side effects of glucocorticoids, prevention and/or treatment of osteoporosis, treatment of chronic fatigue syndrom (CFS), treatment of acute fatigue syndrom and muscle loss following election surgery, stimulation of the immune system, acceleration of wound healing, accelerating bone fracture repair, accelerating complicated fractures, e.g. disctraction osteogenesis, treatment of wasting secondary to fractures, treatment of growth retardation, treating renal failure or insufficiency resulting from growth retardation, treatment of cardiomyopathy, treatment of chronic liver disease, treatment of thrombocytopenia, treatment of Crohn's disease, treatment of short bowel syndrome, treatment of chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treating growth retardation associated with the Prader-Willi syndrome and Turner's syndrome; increasing the growth rate of a patient having partial growth hormone insensitivity syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, treatment of cardiac failure or related vascular dysfunction, treatment of impaired cardiac function, treatment or prevention of myocardial infarction, lowering blood pressure, protection against ventricular dysfunction or prevention of reperfusion events; treatment of adults in chronic dialysis; attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients; treatment of sarcopenia, treatment of wasting in connection with AIDS; improvement in muscle strength, mobility, maintenance of skin thickness, metabolic homeostasis, renal homeostasis in the frail elderly, stimulation of osteoblasts, bone remodelling and cartilage growth, regulation of food intake; stimulation of the immune system in companion animals and treatment of disorder of aging in companion animals, growth promoter in livestock and stimulation of wool growth in sheep, and treatment of metabolic syndrom (syndrome X); treatment of insulin resistance, including NIDDM, in mammals, e.g. humans, and improving sleep quality and correct the relative hyposomatotrapism of senescence due to high increase in REM sleep and a decrease in REM latency. Treatment is also intended to comprise prophylactic treatment.

For use within the present invention a salt of compound I may be formulated with a pharmaceutically acceptable carrier or excipient to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc.

One skilled in this art may formulate the compound in an appropriate manner, and in accordance with accepted practices, such as those disclosed in *Remington's Pharmaceutical Sciences,* 1985 or *Remington's Pharmaceutical Sciences,* Gennaro, ed., Mack Publishing Co., Easton, Pa., 1990, or Remington: The Science and Practice of Pharmacy, 19th Edition (1995). The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

The compositions of this invention are usually adapted for oral administration.

For oral administration a salt of compound I is prepared in a form suitable for oral administration, such as a tablet or capsule. Typically, the compound I is combined with a carrier and molded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions are administered one or more times per day or week. An effective amount of such a pharmaceutical composition is the amount that provides a clinically significant effect. Such amounts will depend, in part, on the particular condition to be treated, age, weight, and general health of the patient, and other factors evident to those skilled in the art.

The pharmaceutical compositions may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., *J Pharm Sci* 73 (1964), 1294–1297, 1984; U.S. Pat. Nos. 4,489,056; and 4,210,644, which are incorporated herein by reference.

The composition is usually presented as a unit dose composition containing 0.01–1000 mg of a salt of compound I in accordance with the invention for oral dosing. Typical dosage for growth hormone releasing effect would vary between 0.1–500 mg, preferably between 0.1 –280 mg per day either once or divided in 2 or 3 doses when administered orally or 2 or 3 times per week or once weekly or once per 14 days.

Preferred unit dosage forms include in solid form, tablets or capsules, in liquid form, solutions, suspensions, emulsions, elixirs or capsules filled with the same, or in form of sterile injectable solutions, or patches, vagitories, vaginal rings or long lasting implantates.

The composition of this invention may be formulated by conventional methods of galenic pharmacy.

Conventional excipients are such pharmaceutically acceptable organic or inorganic carrier substances suitable for parenteral or oral application which do not deleteriously react with the active compound I.

Examples of such carriers are water, salt solutions, alcohols, polyethylene glycols, polyhydroxyethoxylated castor oil, syrup, peanut oil, olive oil, gelatin, lactose, terra alba, sucrose, agar, pectin, acacia, amylose, magnesium stearate, talc, silicic acid, stearic acid, fatty acid monoglycerides and diglycerides, pentaerythritol fatty acid esters, hydroxymethylcellulose and polyvinylpyrrolidone and calcium phosphates.

The pharmaceutical preparations can be sterilized and mixed, if desired, with auxiliary agents, such as binders, lubricants, preservatives, disintegrants, stabilizers, wetting agents, emulsifiers, salt for influencing osmotic pressure, buffers and/or colouring substances and the like, which do not deleteriously react with the active compound. For parenteral application, particularly suitable are injectable solutions or suspensions, preferably aqueous solutions with the active compound dissolved in polyhydroxylated castor oil.

For oral administration, particularly suitable are tablets, dragees, or capsules having talc and/or a carbohydrate carrier or binder or the like, the carrier preferably being lactose or calcium phosphate and/or corn starch and/or potato starch. A syrup, elixir or like can be used when a sweetened vehicle can be employed.

A typical tablet, which may be prepared by conventional tabletting techniques, contains:

| Active compound | 10 mg |
| --- | --- |
| Lactosum | 67.8 mg Ph.Eur. |
| Avicel ® | 31.4 mg |
| Talc | 1.0 mg |
| Magnesii stearas | 0.25 mg Ph.Eur. |

The present invention is further illustrated by the following examples which, however, are not to be construed as limiting the scope of protection. The features disclosed in the foregoing description and in the following examples may, both separately and in any combination thereof, be material for realising the invention in diverse forms thereof.

The salts of compound I according to the invention was synthesized, purified and crystallized as described in the following examples.

EXAMPLES

The compound, (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide, has the structural formula I as shown herein below Formula I

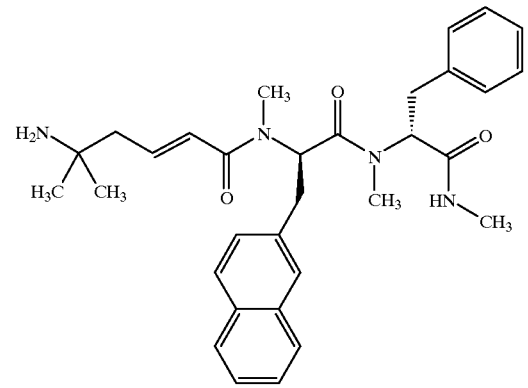

and may be prepared as disclosed in example 1 of WO 97/23508:

Preparation of (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide hydrochloride salt

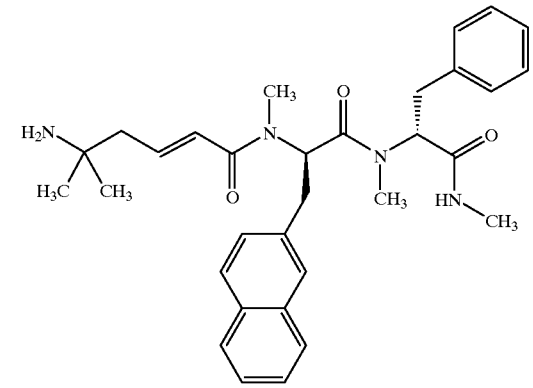

3-Hydroxy-1,1-dimethylpropylcarbamic acid tert-butyl ester

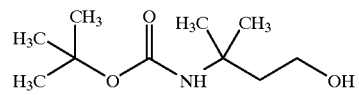

Step A

At 0° C., ethyl chloroformate (1.10 mL, 11.5 mmol) was given dropwise to a solution of 3-tert-butoxycarbonylamino-3-methylbutanoic acid (2.50 g, 11.5 mmol) and triethylamine (1.92 mL, 13.8 mmol) in tetrahydrofuran (10 mL).

The solution was stirred for 40 min at 0° C. The formed precipitate was filtered off and washed with tetrahydrofuran (20 mL). The liquid was immediately cooled to 0° C. A 2M solution of lithium boronhydride in tetrahydrofuran (14.4 mL, 28.8 mmol) was added dropwise. The solution was stirred at 0° C. for 2 h, and then warmed to room temperature over a period of 4 h. It was cooled to 0° C. Methanol (5 mL) was added carefully. 1N Hydrochloric acid (100 mL) was added. The solution was extracted with ethyl acetate (2×100 mL, 3×50 mL). The combined organic layers were washed with saturated sodium hydrogen carbonate solution (100 mL) and dried over magnesium sulfate. The solvent was removed in vacuo. The crude product was chromatographed on silica (110 g) with ethyl acetate/heptane 1:2 to give 1.84 g of 3-hydroxy-1,1-dimethylpropylcarbamic acid tert-butyl ester.

$^1$H-NMR (CDCl$_3$): d 1.33 (s, 6 H); 1.44 (s, 9 H); 1.88 (t, 2 H); 1.94 (br, 1 H); 3.75 (q, 2 H); 4.98 (br, 1 H).

3-(tert-Butoxycarbonylamino)-3-methylbutanal

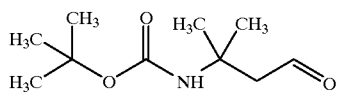

Step B

DMSO (1.22 mL, 17.2 mmol) was added to a solution of oxalyl chloride (1.1 mL, 12.9 mmol) at −78° C. in dichloromethane (15 mL). The mixture was stirred for 15 min at −78° C. A solution of 3-hydroxy-1,1-dimethylpropylcarbamic acid tert-butyl ester (1.75 g, 8.6 mmol) in dichloromethane (10 mL) was added dropwise over a period of 15 min. The solution was stirred at −78° C. for another 15 min. Triethylamine (6.0 mL, 43 mmol) was added. The solution was stirred at −78° C. for 5 min and then warmed to room temperature. The solution was diluted with dichloromethane (100 mL) and extracted with 1N hydrochloric acid (100 mL). The aqueous phase was extracted with dichloromethane (50 mL). The combined organic layers were washed with saturated sodium hydrogen carbonate solution (100 mL) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-(tert-butoxycarbonylamino)3-methylbutanal.

MHz-$^1$H-NMR (CDCl$_3$): d 1.39 (s, 6 H); 1.45 (s, 9 H); 2.85 (d, 2 H); 4.73 (br. 1 H); 9.80 (t, 1 H).

Ethyl (2E)-5-(tert-Butoxycarbonylamino)-5-methylhex-2-enoate

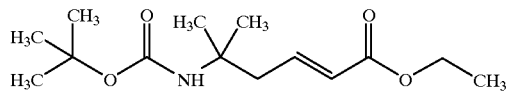

Step C

Triethylphosphonoacetate (1.96 mL, 9.8 mmol) was dissolved in tetrahydrofuran (30 mL). Potassium tert-butoxide (1.10 g, 9.8 mmol) was added. The solution was stirred for 40 min at room temperature. A solution of 3-(tert-butoxycarbonylamino)-3-methylbutanal (1.10 g, 5.5 mmol) in Tetrahydrofuran (6 mL) was added. The solution was stirred at room temperature. for 75 min. It was diluted with ethyl acetate (100 mL) and 1N hydrochloric acid (100 mL). The phases were separated. The aqueous phase was extracted with ethyl acetate (2×50 mL). The combined organic phases were washed with saturated sodium hydrogen carbonate solution (60 mL) and dried over magnesium sulfate. The solvent was removed in vacuo. The crude product was purified by column chromatography on silica (90 g) with ethyl acetate/hepatane (1:4) to give 1.27 g of ethyl (2E)-5-(tert-butoxycarbonylamino)-5-methylhex-2-enoate.

$^1$H-NMR (CDCl$_3$): d 1.30 (s, 6 H); 1.30 (t, 3 H); 1.46 (s, 9 H); 2.62 (d, 2 H); 4.27 (q, 2 H); 4.42 (br, 1 H); 5.88 (d, 1 H); 6.94 (td, 1 H).

(2E)-5-(tert-Butoxycarbonylamino)-5-methylhex-2-enoic acid

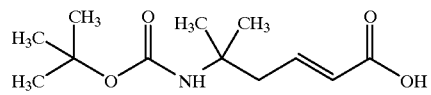

Step D

Ethyl (2E)-5-(tert-butoxycarbonylamino)-5-methylhex-2-enoate (1.233 g, 4.54 mmol) was dissolved in dioxane (20 mL). Lithium hydroxide (0.120 g, 5.00 mmol) was added as a solid. Water (10 mL) was added, until a clear solution was reached. The solution was stirred 16 h at room temperature. The solution was diluted with water (70 mL) and was extracted with tert-butyl methyl ether (2×100 mL). The aqueous phase was acidified with 1N sodium hydrogensulfate solution (pH=1) and was extracted with tert-butylmethylether (3×70 mL). The organic phases were combined and dried over magnesium sulfate. The solvent was removed in vacuo to give 1.05 g of (2E)-5-(tertbutoxycarbonylamino)-5-methylhex-2-enoic acid. The crude product was used for further syntheses.

$_1$H-NMR (DMSO d$_6$): d 1.15 (s, 6 H); 1.35 (s, 9 H); 2.53 (d, 2 H); 5.75 (d, 1 H); 6.57 (br, 1 H); 6.75 (td, 1 H); 12.15 (s, 1 H).

N-Methyl-N-((R)-1-(methylcarbamoyl)-2-phenylethyl)carbamic acid tert-butyl ester

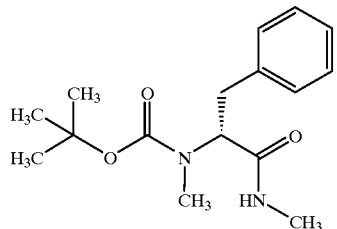

Step E

N-Tert-butoxycarbonyl-N-methyl-D-phenylalanine (1.22 g, 4.4 mmol), 1-hydroxybenzotriazole hydrate (0 59 g, 4.4 mmol) and 1-ethyl-3-(3-dimethyl-aminopropyl)carbodiimid hydrochloride (0.88 g, 4.6 mmol) were dissolved in N,N-dimethylformamide (25 mL) and stirred for 30 min. Methylamine (0.51 g of a 40% solution in methanol, 6.6 mmol)

was added and the mixture was stirred overnight. Methylene chloride (80 mL) and water (100 mL) were added and the phases were separated. The organic phase was washed with sodium hydroxide (20 mL, 1N), sodium hydrogensulfate (50 mL, 10%) and water (50 mL). The organic phase was dried (magnesium sulfate) and the solvent removed in vacuo to afford 1.39 g of N-methyl-N-((R)1-(methylcarbamoyl)-2-phenylethyl)carbamic acid tert-butyl ester.

¹H-NMR (CDCl₃): d 1.25, 1.35 (two s (br), 9H); 2.73–2.94 (m, 7H); 3.30–3.50 (m, 1H); 4.68, 4.90 (two m, 1H); 5.90, 6.12 (two s (br); 1 H); 7.12–7.25 (m, 5H).

(R)-N-Methyl-2-methylamino-3-phenylpropionamide

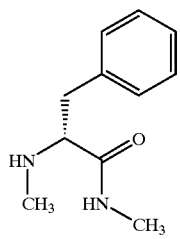

Step F

N-Methyl-N-((R) 1-(methylcarbamoyl)-2-phenylethyl) carbamic acid tert-butyl ester (1.39 g, 7.23 mmol) was dissolved in a mixture of trifluoroacetic acid (5 mL) and methylene chloride (10 mL) and stirred for 45 min. The volatiles were removed in vacuo and the residue was stirred with a mixture of ethyl acetate (100 mL) and water (100 mL). Sodium hydrogen carbonate (50 mL, saturated) was added and the phases were separated. The organic phase was dried (magnesium sulfate) and the solvent removed in vacuo to afford 330 mg of (R)-N-methyl-2-methylamino-3-phenylpropionamide.

¹H-NMR (CDCl₃): d 2.1 (s(br), 3H); 2.32 (s, 3H); 2.77 (dd, 1H); 2.81 (two s, 3H); 3.21 (dd, 1H); 3.32 (dd, 1H); 7.12 (s(br), 1H); 7.20–7.34 (m, 5H).

N-Methyl-N-{(1R)-1-(N-methyl-N-((1R)-1-(methylcarbamoyl)-2-phenylethyl)carbamoyl)-2(2-naphthyl)ethyl}carbamic acid tert-butyl ester

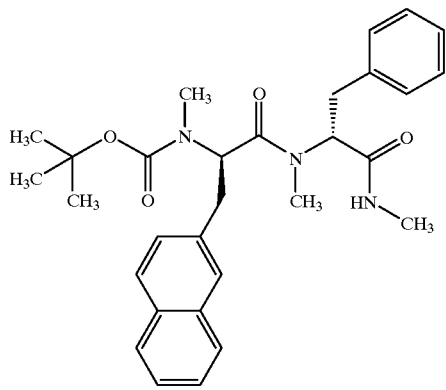

Step G (R)-Tert-butoxycarbonyl-N-methylamino-3-(2-naphthyl) propionic acid (548 mg, 1.66 mmol) was dissolved in methylene chloride (5 mL); 1-hydroxy-7-azabenzotriazole (227 mg, 1,66 mmol) was added along with N,N-dimethylformamide (2 mL). 1-Ethyl-3-(3-dimethylaminopropyl) carbodiimide hydrochloride (351 mg, 1.83 mmol) was added and the solution was stirred for 15 min. (R)-N-Methyl-2-methylamino-3-phenylpropionamide (320 mg, 1.66 mmol) dissolved in methylene chloride (4 mL) and diisopropylethylamine (0.28 mL, 1.66 mmol) were added and the mixture was stirred overnight. Methylene chloride (50 mL) was added and the organic phase was washed with water (100 mL), sodium hydrogensulfate (50 mL, 5%) and sodium hydrogen carbonate (50 mL, saturated). The organic phase was dried (magnesium sulfate) and the solvent removed in vacuo. The residue was chromatographed (silica, 2×45 cm) using ethylacetate/methylene chloride (1:1) to afford 604 mg of N-methyl-N-{(1R)-1-(N-methyl-N-((1R)-1-(methylcarbamoyl)-2-phenylethyl)carbamoyl)-2-(2-naphthyl)ethyl}carbamic acid tert-butyl ester.

¹H-NMR (CDCl₃): d 1.05, 1.31, 1.56 (three s, 9H); 2.28–3.37 (several m, 13 H); 5.04, 5.17, 5.29, 5.48 (four dd, 2H); 7.05–7.79 (m, 12 H).

(2R)-N-Methyl-2-methylamino-N-((1R)-1-(methylcarbamoyl)-2-phenylethyl)-3-(2-naphthyl) propionamide

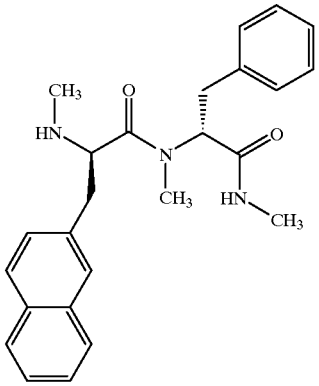

Step H

N-Methyl-N-{(1R)-1-(N-methyl-N-((1R)-1-(methylcarbamoyl)-2-phenyl-ethyl)carbamoyl)-2-(2-naphthyl)ethyl}carbamic acid tert-butyl ester (600 mg, 1.19 mmol) was stirred in trifluoroacetic acid/methylene chloride (1:1, 5 mL) for 10 min and the volatiles were removed in vacuo. The residue was stripped with diethylether (2×5 mL) and dissolved in methanol (2 mL) and mixed with sodium hydrogen carbonate (10 mL) and ethylacetate (15 mL). The organic phase was separated and dried (magnesium sulfate) to afford 420 mg of (2R)-N-methyl-2-methylamino-N-((1R)-1-(methylcarbamoyl)-2-phenylethyl)-3-(2-naphthyl) propionamide.

¹H-NMR (CDCl₃): (selected values) d 1.69 (s, 3H); 2.08 (d, 3H); 2.54 (s, 3H); 2.76 (dd, 1H); 2.92 (dd, 1H), 3.12 (dd, 1H), 3.31 (dd, 1H), 3.72 (dd, 1H), 4.95 (q (br), 1H); 5.50 (dd, 1H).

((3E)-1,1-Dimethyl-4-(N-methyl-N-((1R)-1-(N-methyl-N-((1R)-1-(methylcarbamoyl)-2-phenylethyl)carbamoyl)-2-(2-naphthyl)ethyl)carbamoyl)but-3-enyl)carbamic acid tert-butyl ester

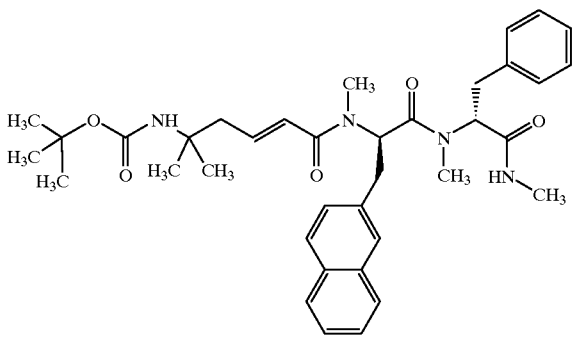

Step I (2E)-5-(tert-Butyloxycarbonylamino)-5-methylhex-2-enoic acid (200 mg, 0.82 mmol), 1-hydroxy-7-azabenzotriazole (112 mg, 0.82 mmol) and 1-ethyl-3-(3-dimethylaminopropyl)-carbodiimide hydrochloride (173 mg, 0.90 mmol) were dissolved in a mixture of methylene chloride (10 mL) and N,N-dimethylformamide (1 mL) and stirred for 15 min. N-Methyl-2-methylamino-N-((1R)-1-(methylcarbamoyl)-2-phenylethyl)-3-(2-naphthyl)propionamide (332 mg, 0.82 mol) dissolved in methylene chloride (5 mL) and diisopropylethylamine (0.14 mL) were added and the mixture was stirred overnight under nitrogen atmosphere. The mixture was diluted with methylene chloride (50 mL), washed with water (50 mL), sodium hydrogen carbonate (30 mL, saturated), and sodium hydrogensulfate (30 mL, 5%). The phases were separated and the organic phase was dried with magnesium sulfate and evaporated in vacuo. The residue was chromatographed (silica, 2×40 cm) to afford 450 mg of ((3E)-1,1-dimethyl-4-(N-methyl-N-((1R)-1-(N-methyl-N-((1R)-1-(methylcarbamoyl)-2-phenylethyl)carbamoyl)-2-(2-naphthyl)ethyl)carbamoyl)but-3-enyl)-carbamic acid tert-butyl ester.

$^1$H-NMR (CDCl$_3$): (selected values) d 1.20, 1.22, 1.24, 1.30, 1.41, 1.55 (six s, 15 H), 4.30, 4.40 (two s (br), 1H); 5.08, 5.18, 5.32, 5.60, 5.87 (five dd, 2H); 6.05 (dd, 1H); 6.75 (m, 1H).

Step J ((3E)-1,1-Dimethyl-4-(methyl-((1R)-1-(methyl-((1R)-1-(methylcarbamoyl)-2-phenylethyl)carbamoyl)-2-(2-naphthyl)ethyl)carbamoyl)but-3-enyl)carbamic acid tert-butyl ester (403 mg, 0.63 mmol) was stirred in a mixture of trifluroacetic acid (4 mL) and methylene chloride (4 mL) for 10 min. The volatiles were removed in vacuo and the crude product was chromatograped on silica (400 g) using a mixture of methylene chloride, ethanol and ammonia (25% in water) (80/18/2) as eluent. The isolated product was dissolved in 3M hydrochloric acid in ethyl acetate and evaporated, then redissolved in methylene chloride and evaporated twice to afford 140 mg of the title compound.

$^1$H-NMR (CDCl$_3$): d 1.05, 1.10, 1.15, 1.16 (fours, 6H); 2.07 (s (br); 3H); 5.12, 5.32, 5.40, 5.60, 5.91 (five dd, 2H); 6.05, 6.14 (two d, 1H); 6.80 (m, 1H)

HPLC: R$_t$=29.02 min (Method A1)

ESMS: m/z=529 (100%)(M+H)$^+$.

EXAMPLE 1

Synthesis of Compound I,hemi fumarate
(Hereinafter Compound I,hfum)

20,5 g (MW: 528,7 g) of compound I raw product (contains app. 10–20% residual solvent) is dissolved in 200 ml 2-propanol at 45° C. and the temperature is raised to 75° C. 2,0 Og (MW: 116, 1 g; 17 mmol) of fumaric acid is dissolved in 100 ml of 2-propanol at 75° C. and slowly added. The reaction temperature is kept at 75° C. It is important not to overdose the amount of fumaric acid too much, as this will have a negative effect on the yield and purity. Seeding crystals are added if precipitation has not occurred within 1 h. Stirring is continued overnight at 70–75° C. The next day the reaction mixture equilibrates over app. 4 h to r.t. by removing the heating facility. The mixture is cooled to 0–5° C. and kept for 2 h at that temperature. The suspension is easily filtered and the filter cake is washed with cold 2-propanol. The product is dried overnight at 40° C. in a vacuum shelf drier leaving 18, 1 g (89% calculated from fumaric acid) of compound I,hfum (MW: 586,7 g) as white crystals.

EXAMPLE 2

Synthesis of Compound I,hemi fumarate monohydrate 50,8 g of compound I raw product (contains app. 10–20% residual solvent) is dissolved in 500 ml of ethanol (or 2-propanol) at 70° C. and 5.4 g fumaric acid (47 mmol) dissolved in 70° C. 250 ml of ethanol (or 2-propanol) is added. The heating facility is removed and the mixture is allowed to equilibrate to r.t. overnight. Precipitation occurs around 60° C. after addition of seeding crystals. The next day the suspension is cooled to 0–5° C. for 2 h and filtered to give small crystals, that are very difficult to filter. The filter cake is washed with cold ethanol (or 2-propanol) and dried overnight at 40° C. in a vacuum shelf drier leaving 35,3 g (65% calculated from fumaric acid) of compound I,hfum monohydrat as white crystals.

A similar experiment was performed in 2-propanol, with same result.

Exposure of the anhydrous form of compound I,hfum to high humidity, e.g. 10 weeks at 98% RH, produced the hydrous form.

EXAMPLE 3

Synthesis of Compound I,L-(+)mandelate 2,0 g of compound I raw product (contains app. 10–20% residual solvent) is dissolved in 10 ml of acetone. 0,58 g (MW: 152,2; 3,8 mmol) L-mandeleic acid is dissolved in 10 ml of acetone and added. The mixture is heated to reflux. Precipitation occurs within 5 min after addition of seeding crystals. Reflux is kept for 2 h. The heating facility is removed and the suspension is equilibrates to r.t. The suspension is filtered. The filter cake is washed with acetone. The product is dried overnight at 40° C. in a vacuum shelf drier leaving 1,5 g of (58% calculated from L-(+)mandeleic acid) compound I,L-(+)mandelate (MW: 680,8 g) as white crystals.

EXAMPLE 4

Synthesis of Compound I,D-(−)mandelate 7,9 g of compound I raw product (contains app. 10–20% residual solvent) is dissolved in 160 ml acetone. 2,3 g (MW: 152,2;15 mmol) D-mandeleic acid is dissolved in 40 ml acetone and added. The mixture is heated to reflux. Precipitation occurs within 10 min after addition of seeding crystals. Reflux is kept for 3h. The heating facility is removed and the suspension is equilibrated to r.t. The suspension is filtered. The filter cake is washed with acetone. The product is dried overnight at 40° C. in a vacuum shelf drier leaving 6,6 g (65% calculated from D-(–)mandeleic acid) of compound I, D-(–)mandelate (MW: 680,8 g) as white crystals.

EXAMPLE 5

Synthesis of Compound I,maleate 0,44 g maleic acid is dissolved in 10 ml of acetone at reflux. 2,0 g compound I raw product (contains app. 10–20% residual solvent) is dissolved in10ml of acetone and added. The mixture is stirred overnight at 45° C. Crystallisation has occurred during the night. The heating facility is removed and the mixture is allowed to equilibrate to r.t. The suspension is filtered. The filter cake is washed with acetone. The product is dried overnight at 40° C. in a vacuum shelf drier leaving 1,57 g (65% calculated from maleic acid) of compound I,maleate (MW: 644,8 g) as white crystals.

What is claimed is:

1. (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide,hemi fumarate.

2. (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide,hemi fumarate monohydrate.

3.(2E)-5-amino-5-methylhex-2-enoic acid N-methyl-N-((1R)-1-(N-methyl-N-((1R)-1--(methylcarbamoyl)-2-phenylethyl)carbamoyl)-2-(2-naphthyl)ethyl)amide,L(+)-mandelate.

4. A pharmaceutical composition comprising the hemifumarate salt, the hemifumarate monohydrate salt or the L(+)-mandelate salt of (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide, together with a pharmaceutically acceptable carrier or diluent.

5. The pharmaceutical composition according to claim 4 in the form of a unit dosage form containing about 0.01–1000 mg of the salt.

6. A method for stimulating the release of growth hormone in a patient comprising administering to the patient a therapeutically effective amount of the hemifumarate salt, the hemifumarate monohydrate salt or the L(+)-mandelate salt of (2E)-5-amino-5-methylhex-2-enoic acid N-methyl-N-((1R)-1-(N-methyl-N-((1R)-1-(methylcarbamoyl)-2-phenylethyl) carbamoyl)-2-(2-naphthyl)ethyl)amide.

7. The compound of claim 1 having an aqueous solubility of at least about 5 mg/ml and a hygroscopicity of less than about 8 at 98% RH.

8. The compound of claim 2 having an aqueous solubility of at least about 5 mg/ml and a hygroscopicity of less than about 8 at 98% RH.

9. The compound of claim 3 having an aqueous solubility of at least about 5 mg/ml and a hygroscopicity of less than about 8 at 98% RH.

10. The composition of claim 4, wherein the salt has an aqueous solubility of at least about 5 mg/ml and a hygroscopicity of less than about 8 at 98% RH.

11. The method of claim 6, wherein the salt has an aqueous solubility of at least about 5 mg/ml and a hygroscopicity of less than about 8 at 98% RH.

* * * * *